United States Patent
Hakimimehr (10) Patent No.: US 11,806,072 B2
(45) Date of Patent: Nov. 7, 2023

(54) METHOD AND APPARATUS FOR TREATING PERIPHERAL OLFACTORY DYSFUNCTION

(71) Applicant: Dorna Hakimimehr, Redwood City, CA (US)

(72) Inventor: Dorna Hakimimehr, Redwood City, CA (US)

( * ) Notice: Subject to any disclaimer, the term of this patent is extended or adjusted under 35 U.S.C. 154(b) by 0 days.

(21) Appl. No.: 18/047,786

(22) Filed: Oct. 19, 2022

(65) Prior Publication Data

US 2023/0149068 A1 May 18, 2023

Related U.S. Application Data

(60) Provisional application No. 63/264,074, filed on Nov. 15, 2021.

(51) Int. Cl.

| | |
|---|---|
| *A61B 18/14* | (2006.01) |
| *A61B 18/02* | (2006.01) |
| *A61B 34/20* | (2016.01) |
| *A61B 18/18* | (2006.01) |
| *A61B 18/00* | (2006.01) |
| *A61B 90/00* | (2016.01) |

(Continued)

(52) U.S. Cl.
CPC .......... *A61B 18/1485* (2013.01); *A61B 18/02* (2013.01); *A61B 34/20* (2016.02); *A61B 18/1815* (2013.01); *A61B 2018/00327* (2013.01); *A61B 2018/00577* (2013.01); *A61B 2018/00982* (2013.01); *A61B 2018/2211* (2013.01); *A61B 2090/306* (2016.02); *A61B 2090/3612* (2016.02); *A61B 2090/3614* (2016.02)

(58) Field of Classification Search
CPC ..... A61B 18/14; A61B 18/1485; A61B 18/02; A61B 18/06; A61B 18/0218; A61B 2018/00327; A61B 2018/00577; A61B 2018/0262
See application file for complete search history.

(56) References Cited

U.S. PATENT DOCUMENTS

| | | | |
|---|---|---|---|
| 2011/0040144 A1 | 2/2011 | Jackson | |
| 2014/0221456 A1* | 8/2014 | Schwob | A61P 11/00 435/375 |
| 2016/0317621 A1* | 11/2016 | Bright | A61B 90/30 |

(Continued)

OTHER PUBLICATIONS

Gage et al. "Experimental Cryosurgery Investigations in Vivo." Cryobiology, 59(3), 229 (2009).

(Continued)

*Primary Examiner* — Khadijeh A Vahdat
(74) *Attorney, Agent, or Firm* — Levine Bagade Han LLP (57) ABSTRACT

Method and apparatus for treating peripheral olfactory dysfunction are described herein. One method may include introducing a treatment device into a nasal cavity of the patient, the treatment device having a proximal end, a distal end, an elongated shaft therebetween, and a treatment end effector disposed on or near the distal end. The distal end of the treatment device may be advanced into proximity of a cribriform plate within the nasal cavity and at least one olfactory neuron may be ablated through the cribriform plate via the treatment end effector to reduce at least one symptom of olfactory dysfunction.

30 Claims, 9 Drawing Sheets

(51) Int. Cl.
  *A61B 18/22* (2006.01)
  *A61B 90/30* (2016.01)

(56) References Cited

U.S. PATENT DOCUMENTS

2017/0231474 A1* 8/2017 Saadat .................. A61B 18/02
                                                    600/107
2020/0038134 A1  2/2020 Lin et al.

OTHER PUBLICATIONS

Hwang et al. "Cryosurgical Posterior Nasal Tissue Ablation for the Treatment of Rhinitis." International Forum of Allergy and Rhinology, 7(10), (2017).
Schwob "Neural Regeneration and the Peripheral Olfactory System." The Anatomical Record. 269, 33-49 (2002).
Whittaker "Degeneration and Regeneration of Nerves Following Cryosurgery." Department of Oral Biology, 55, 595-600 (1974).
Albu et al. "The Influence of Spray Cryotherapy on Wound Healing Following Endoscopic Sinus Surgery in Chronic Rhinosinusitis." Laryngoscope, 126, 25-32 (2016).
Flippiadis et al. "The Role of Ablation in Cancer Pain Relief." Current Oncology Reports, 21:105 (2019).
Morrissey et al. "The Role of Surgery in the Management of Phantosmia." The Laryngoscope 126, 575-578 (2016).
Rezaeian "Outcome of Spray Cryotherapy Plus Functional Endoscopic Sinus Surgery on Management of Healing in Nasal Polyposis." Journal of Otolaryngology, (2017).

\* cited by examiner

METHOD AND APPARATUS FOR TREATING PERIPHERAL OLFACTORY DYSFUNCTION

CROSS-REFERENCE TO RELATED APPLICATIONS

This application claims the benefit of priority to U.S. Prov. App. 63/264,074 filed Nov. 15, 2021, which is incorporated herein by reference in its entirety.

BACKGROUND OF THE INVENTION

The olfactory system is generally comprised of olfactory neurons embedded within an epithelium layer that covers part of the nasal cavity including over the cribriform plate. The location of the olfactory epithelium exposes it to environmental odors that trigger the primary olfactory neurons to send signals to the central nervous system via the olfactory bulb. While the location of the olfactory epithelium provides for easy access to airflow and odors it also exposes it to environmental toxins, infectious diseases or trauma that could results in its dysfunction. To solve for this vulnerability, the olfactory system has developed a unique ability for regeneration. Experimental studies have shown the extraordinary capacity of the olfactory epithelium to regenerate following injury (Schwob, 2002).

Olfaction dysfunction can present in different ways: such as decreased sensitivity, distorted quality of an odorant stimulation, and perceived order when no odor is present (phantosmia). Olfactory dysfunction can be a result of either dysfunction of the olfactory neurons (peripheral dysfunction) or can be triggered through the central nervous system without the involvement of the primary neurons (central dysfunction).

No definitive treatment for olfactory dysfunction exists today. Strategies such as scent therapy, saline irrigation, local cocaine administration, antidepressant and anti-inflammatory medication are commonly used with limited benefits. New strategies to accelerate olfactory neural regeneration are currently the subject of research in treating peripheral olfactory dysfunction. In the only surgical treatment for olfactory dysfunction Leopold et al. performed excision of the olfactory epithelium through an intra nasal procedure (Leopold et al., 1991).

The results of the work performed by (Leopold et al., 1991) has shown that after removing the olfactory epithelium in patients with peripheral olfactory dysfunction, such as phantosmia, a new functional epithelium regenerates, resolving the dysfunction. However, the surgical procedure to remove the olfactory mucosa is technically difficult to perform and carries the risk of cerebrospinal fluid (CSF) leak due to potential damage to cribriform plate, compromised efficacy due to incomplete removal of the epithelium and general surgical complications (Morrissey et al., 2016).

Nerve ablation (destruction) is a minimally invasive procedure commonly used to treat pain (Filippiadis et al., 2019). In this procedure, all or part of a nerve is ablated to interrupt the pain signal resulting in pain relief (Gage et al., 2009). Different methods of nerve ablation exist, for example it can be done by heat, such as radiofrequency or microwave ablation, cold such as cryoablation, chemicals (such as ethanol, phenol, and zinc sulfate), and electromagnetic field such as pulsed radiofrequency. Cryo nerve ablation is reversible, meaning the ablated nerves regenerate over time and regain their original function (Whittaker, 1974).

More specifically, John Hunter in 1777 observed that upon exposing tissue to freezing temperature, tissue necrosis occurs followed by healing and regeneration. Local tissue freezing, or cryosurgery has been commercially available since the 1960s and the advances of the technology has resulted in its widespread use especially in causing reversible destruction of nerves or cryoneurolysis in treatment of pain. Cryoneurolysis has been used to treat head and neck disorders such as vasomotor rhinitis (Hwang et al., 2017), nasal polyposis (Rezaeian, 2018) and mucosal healing post functional endoscopic sinus surgery (Albu et al., 2016), demonstrating its safety and efficacy.

The present invention intends to teach methods and minimally invasive apparatus to treat peripheral olfactory dysfunction by intentionally creating localized neurolysis of the olfactory neurons, prompting neuroepithelium regeneration and therefore treating the dysfunction. At first glance, this method might be considered counter intuitive as recent efforts in treating olfactory dysfunction have focused on assisting regenerative processes, making destruction and ablation of olfactory neurons counter to such effort. However, the methods and apparatus disclosed intends to cause regeneration of neurons by first reversibly destroying malfunctioning neurons without causing injury to anatomic structures therefore setting the stage for regeneration of functional neurons. Methods and apparatus disclosed are minimally invasive procedures therefore the risk of intensive surgery under general anesthesia is eliminated making this treatment modality safer than the alternative surgical procedure.

SUMMARY OF THE INVENTION

The olfactory mucosa (OM) includes a specialized olfactory epithelium and the lamina propria, in which Bowman glands, bundles of olfactory neurons and ensheathing glia are present. Peripheral olfactory dysfunction such as phantosmia is thought to be due to the dysfunction of the olfactory neurons, leading to an inability to form a complete picture of the odor and hence the erroneous interpretation of the odor centrally.

The devices and methods are disclosed for treating peripheral olfactory dysfunction by ablating the olfactory neurons to cause reversible destruction prompting regeneration of the olfactory neurons and olfactory epithelium, "resetting" the olfactory function.

The size of the olfactory mucosa can vary among individuals, however all primary olfactory neurons leaving the epithelium go through the cribriform plate, a sieve-like bony structure, to reach the olfactory bulb, making it a specifically suitable target for ablation. In one embodiment of the present invention the OM over the cribriform plate is the ablation target in order to ablate all primary neurons.

The devices disclosed used to ablate olfactory neurons may be comprised of an elongated shaft having a proximal end and a distal end, where the distal end of the device can navigate through the nasal cavity under endoscopic visualization. The proximal end of the device is used to control the navigation and the ablation procedure. In one embodiment of the above configuration the distal and proximal end of the device are in fluid communication (e.g., liquid and/or gas).

In another embodiment of the device, the distal end of the device is designed to be atraumatic to the nasal mucosa as it navigates through the nasal cavity or when it reaches its target tissue.

In one embodiment, the distal end can have a collapsed and an expanded configuration so that during navigation to the target site the distal end is in the collapsed state and is expanded once it reaches the target tissue to cover the surface area of the OM or conform to its form without compromising its ability to navigate through tight spaces. Upon completion of the ablation procedure the distal end is collapsed before the device is removed from the nasal cavity.

In another embodiment, the ablation device is a cryogenic device. In this configuration the distal end is placed directly adjacent to the OM. The temperature of the distal end is then reduced to temperatures in the range of, e.g., −20° C. to −100° C., freezing the adjacent tissue causing neurolysis. The tissue may be kept frozen for a period of time before the temperature of the distal end is returned to environmental temperature, thawing the tissue at the same time. The freeze and thaw cycle can be carried out multiple times to produce the desired effect. The preferred period of time for keeping tissue frozen is from about 10 seconds to about 120 seconds or more preferably between 10 seconds to about 60 seconds.

In another embodiment, the device is a cryogenic device that uses the Joules-Thomson (JT) effect to produce the ultra-low temperature. In such a configuration the high-pressure refrigerant gas, liquid, or a mixture thereof is injected through an internal lumen to the distal end of the device such that when the gas leaves the internal lumen at the proximity of the distal end, it expands into an outer lumen causing a drop in temperature. The exhaust gas is then released back to the environment. In another embodiment, the refrigerant gas used to produce the JT effect can also be used to expand the distal end of the device when the distal end is designed to be expandable.

In another embodiment, the refrigerant gas or liquid is directly sprayed on the target tissue. In this embodiment the proximal end of the device, the shaft and the distal end are in fluid communication (e.g., liquid and/or gas). The proximal end of the device is connected to a source of pressurized refrigerant gas, liquid, or a mixture thereof. The device shaft and distal end are designed so that they can navigate through the nasal cavity to reach the target tissue. Once in place, the refrigerant gas or liquid is sprayed on the tissue through the distal end. The distal end is designed to optimize spray pattern and size.

In another embodiment another principle other than the JT system is used to cool the distal end of the device in order to freeze tissue.

In another embodiment the cryogenic device uses nitrous oxide as the refrigerant gas. In another embodiment the cryogenic device uses carbon dioxide as the refrigerant gas. In another embodiment the cryogenic device uses any chlorofluorocarbon, hydrochlorofluorocarbon, hydrofluorocarbon or any mixtures thereof as refrigerant. In yet another embodiment the cryogenic device uses liquid nitrogen as refrigerant.

In one embodiment, the cryogenic device is designed so that the freezing depth of the device matches the thickness of the OM to prevent damage to the underlying bone. The preferred freezing depth is between 100 µm to 5 mm or more preferably between 100 µm to 3 mm.

In another embodiment the device used to ablate olfactory neurons uses radiofrequency energy for ablation. In yet another embodiment the device used to ablate olfactory neurons uses pulsed radiofrequency energy for ablation. In yet another embodiment the device used to ablate olfactory neurons uses microwave energy for ablation. In yet another embodiment the device used to ablate olfactory neurons uses laser for ablation.

In another embodiment one point or multiple points of the shaft is malleable so that the angle between the distal end and the shaft can be controlled to allow for the exact positioning of the distal end or to place the distal end in parallel to the target tissue. Such an angle can be controlled in-situ during operation, or the angle can be adjusted according to the patient's anatomy prior to the start of the operation. In another embodiment, the distal end of the device is malleable.

In another embodiment the ablation device operates under endoscopic visualization. In another embodiment the device comprises a visualization component eliminating the need for using another visualization device such as endoscope.

In one method of use, a patient may be selected for the operation to be treated for peripheral olfactory dysfunction upon consultation with physician. The device is then navigated through the nasal cavity of the patient under endoscopic visualization. Once the distal end of the device is placed in proximity of the OM, especially OM over the cribriform plate, an ablation mechanism is triggered resulting in ablation of tissue and substantially all olfactory neurons. Once the ablation procedure is completed the device is navigated out of the nasal cavity. The patient will lose sense of smell for a period of time. Once the ablated neurons regenerate sense of smell may return without the dysfunction.

One variation of a method for treating peripheral olfactory dysfunction in a patient may generally comprise introducing a treatment device into a nasal cavity of the patient, the treatment device having a proximal end, a distal end, an elongated shaft therebetween, and a treatment end effector disposed on or near the distal end. The distal end of the treatment device may be advanced into proximity of a cribriform plate within the nasal cavity and at least one olfactory neuron may be ablated through the cribriform plate via the treatment end effector to reduce at least one symptom of olfactory dysfunction.

Another variation of a method for treating peripheral olfactory dysfunction in patient may generally comprise introducing a treatment device into a nasal cavity of the patient, the treatment device having a proximal end, a distal end, an elongated shaft therebetween, and a spray component disposed on or near the distal end. The distal end of the treatment device may be advanced into proximity of at least one olfactory neuron associated with olfactory mucosa and at least one chemical may be sprayed to ablate the at least one olfactory neuron to reduce at least one symptom of olfactory dysfunction.

Another variation of a method for treating peripheral olfactory dysfunction in patient may generally comprise introducing a treatment device into a nasal cavity of the patient, the treatment device having a proximal end, a distal end, an elongated shaft therebetween, and an injection instrument disposed on or near the distal end. The distal end of the treatment device may be advanced into proximity of at least one olfactory neuron associated with olfactory mucosa and at least one chemical may be injected to ablate the at least one olfactory neuron to reduce at least one symptom of olfactory dysfunction.

BRIEF DESCRIPTION OF THE DRAWINGS

FIG. 2 illustrates the position of the olfactory apparatus within a nasal cavity and a schematic of an example of the device, where

DETAILED DESCRIPTION OF THE INVENTION

Figure 1A:
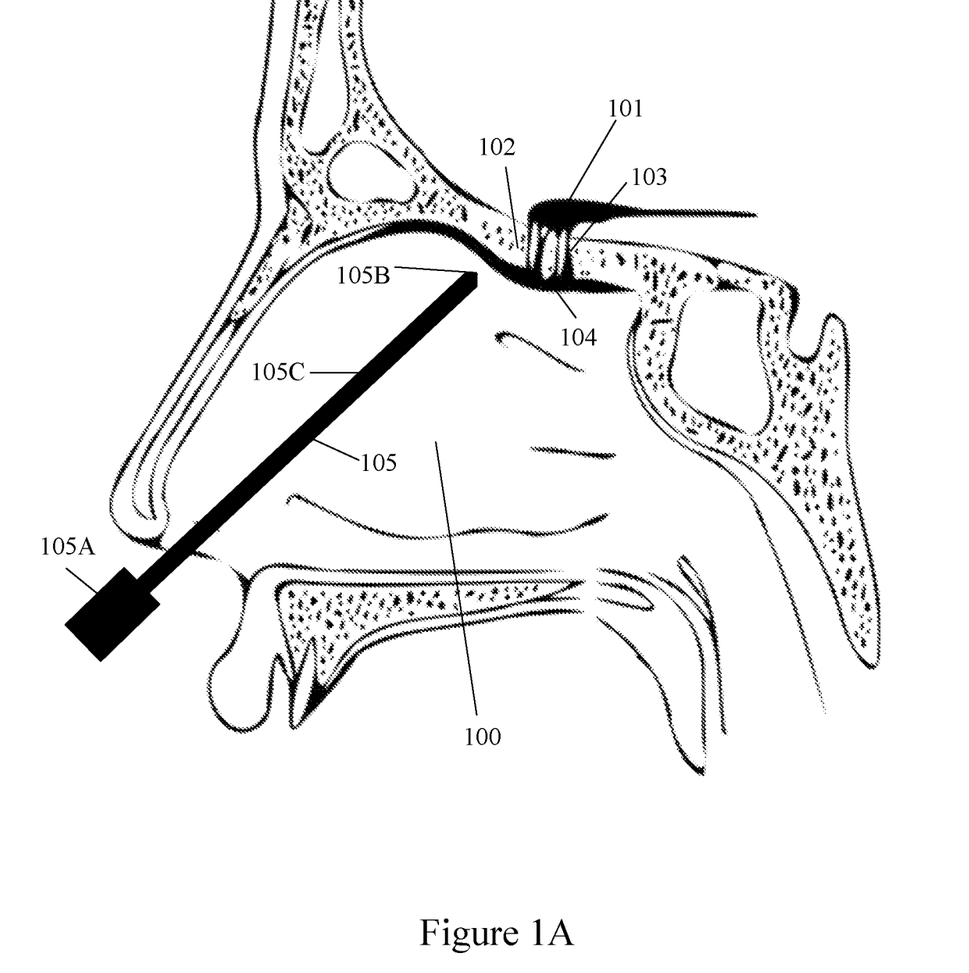
FIG. 1A illustrates the position of the olfactory apparatus within nasal cavity and a schematic of an example of the device.

FIG. 1A shows patient anatomy, including nasal cavity 100, olfactory bulb 101, cribriform plate 102, primary olfactory neurons 103, and olfactory mucous membrane 104. Device 105 may be comprised of proximal end 105A connected to the distal end 105B by elongated shaft 105C. The distal end 105B is maneuvered through the nasal cavity 100 to reach the proximity of olfactory mucosa 104 covering the cribriform plate 102. The distal end 105B includes a treatment end effector which is used to treat the olfactory dysfunction, for example by ablating substantially all primary olfactory neurons of the olfactory mucosa 104.

In one embodiment the distal end 105B is designed to be atraumatic to the structures it encounters.

In another embodiment the device 105 has a cryogenic component. In other embodiments the treatment end effector of device 105 uses radiofrequency, pulsed radiofrequency, laser, microwave, or other methods to ablate olfactory neurons 103.

In another embodiment the device 105 has a cryogenic component that uses compressed gas, liquid, or a mixture thereof as refrigerant. In this embodiment the expansion of the refrigerant gas inside device 105 causes the cooling of the distal end 105B.

In another embodiment the dimensions of device 105 are such that it can operate within the confines of nasal cavity 100 in conjunction with a visualization device such as nasal endoscope. For example, the device 105 may have a shaft with a length ranging from, e.g., 4 cm to 12 cm. The diameter of the distal end of the device is such to provide easy navigation to OM and can range in diameter from, e.g., 0.5 mm to 5 mm, and from 2 mm to 30 mm in length.

Figure 1B:
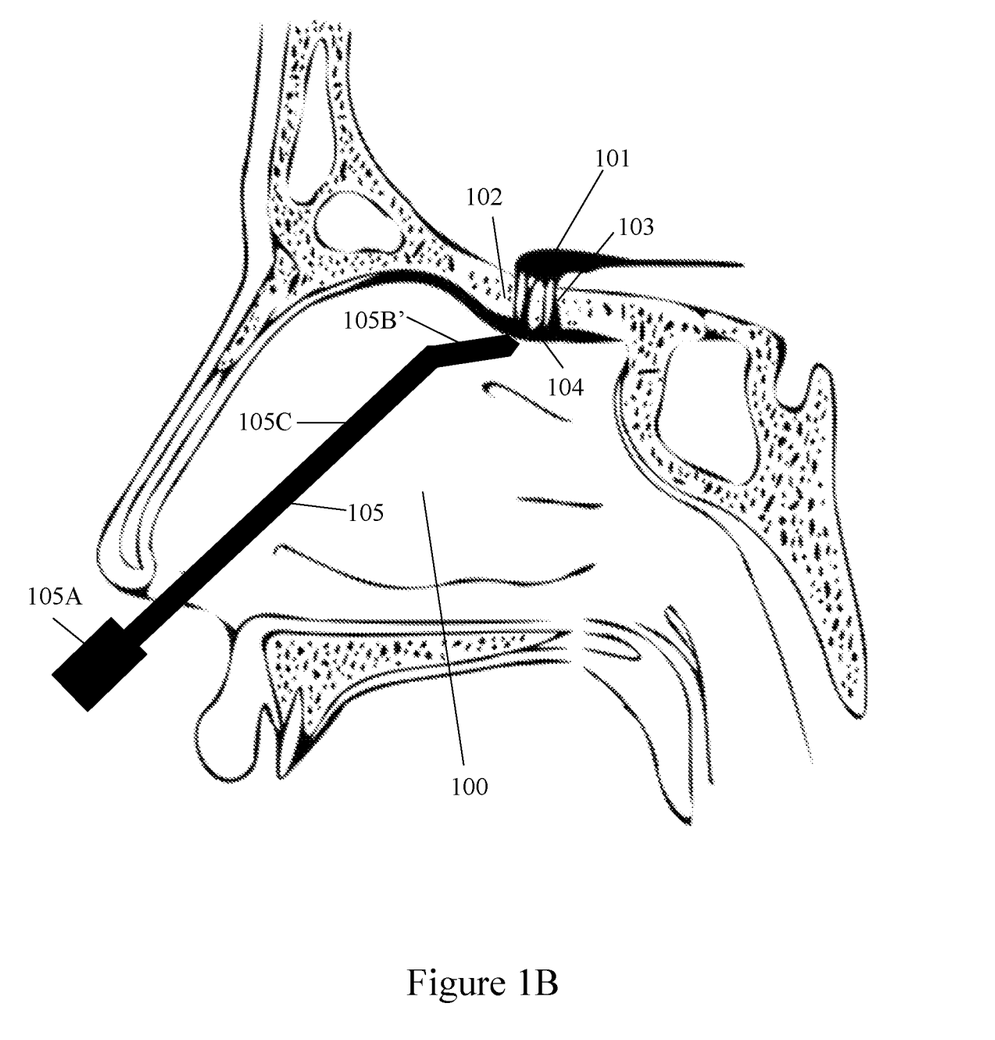
FIG. 1B illustrates the position of the olfactory apparatus within nasal cavity and a schematic of the device where the distal end is positioned at an angle in relation to the device shaft.

FIG. 1B shows patient anatomy, including nasal cavity 100, olfactory bulb 101, cribriform plate 102, primary olfactory neurons 103, and olfactory mucous membrane 104. Device 105 may be comprising proximal end 105A connected to the distal end 105B' by elongated shaft 105C. The distal end 105B' sits at an angle relative to shaft 105C making it easier for the device to contact the target tissue. The shaft 105C may accordingly include a proximal portion extending longitudinally and a distal portion which is angled relative to the proximal portion about an inflection point such as a curved or bent portion or pivoted portion where the angle may range from, e.g., 5 to 30 degrees.

In another embodiment, all or part of shaft 105C is malleable allowing for adjusting the angle between distal end 105B and shaft 105C. In another embodiment, distal end 105B' is malleable.

Figure 1C:
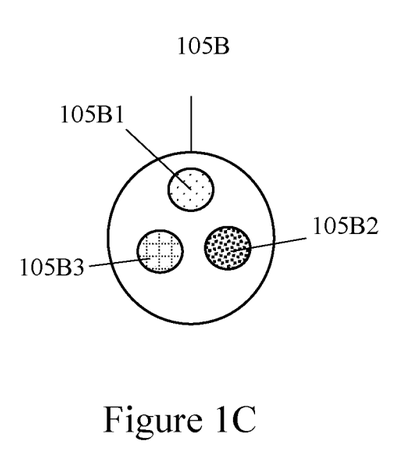
FIG. 1C is a schematic of cross section view of the distal end of an example of the device.

FIG. 1C shows the cross section of distal end 105B of another embodiment where distal end 105B comprises ablation effector 105B1, illumination component 105B2 (e.g., optical fibers coupled to a light source or conductive wires coupling a light emitter such as an LED located in the distal end 105B to a power supply) and imaging component 105B3 (e.g., optical fibers for transmitting images or conductive wires coupled to an imager such as a CCD or CMOS imager, etc. located in the distal end 105B). This embodiment of device 105 makes it possible for device 105 to complete the ablation procedure without the need of an additional visualization instrument. In yet another embodiment device 105 includes a component to facilitate its navigation using various visualization modalities for example facilitating its use with commercially available navigation systems such as the StealthStation™ ENT (Medtronic, Inc.).

Figure 1D:
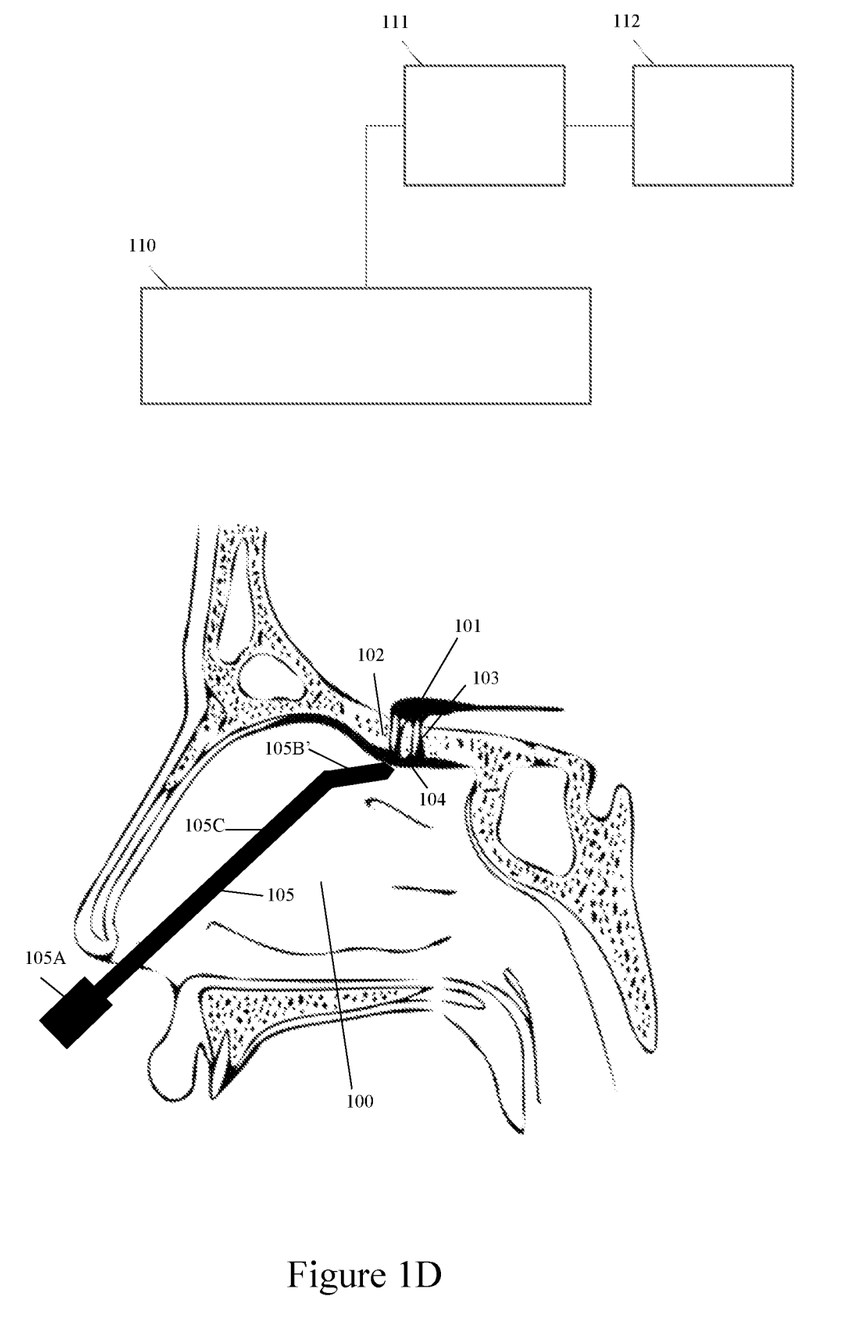
FIG. 1D illustrates an example of a navigation system being used to accurately guide the distal end of the device within the nasal cavity.

An example is illustrated in FIG. 1D showing how a commercially available navigation system may be used to provide guidance in accurately positioning the distal end 105B of the device against a preselected tissue region or nerve fiber for treatment. The example shown illustrates how a camera or imaging system 110 may be positioned into proximity of the patient's head and nasal cavity 100. The imaging system 110 may be in communication with a controller 111 which may be under the control of the practitioner. A display and/or user interface 112 may also be available for displaying the images of the nasal cavity 110 and its anatomical features obtained by the imaging system 110. The images may be displayed 112 as the device and distal end 105B are navigated within the nasal cavity 100 allowing for the practitioner to guide the distal end 105B into proximity and/or against the preselected tissue region or nerve fiber for treatment.

Figure 2A:
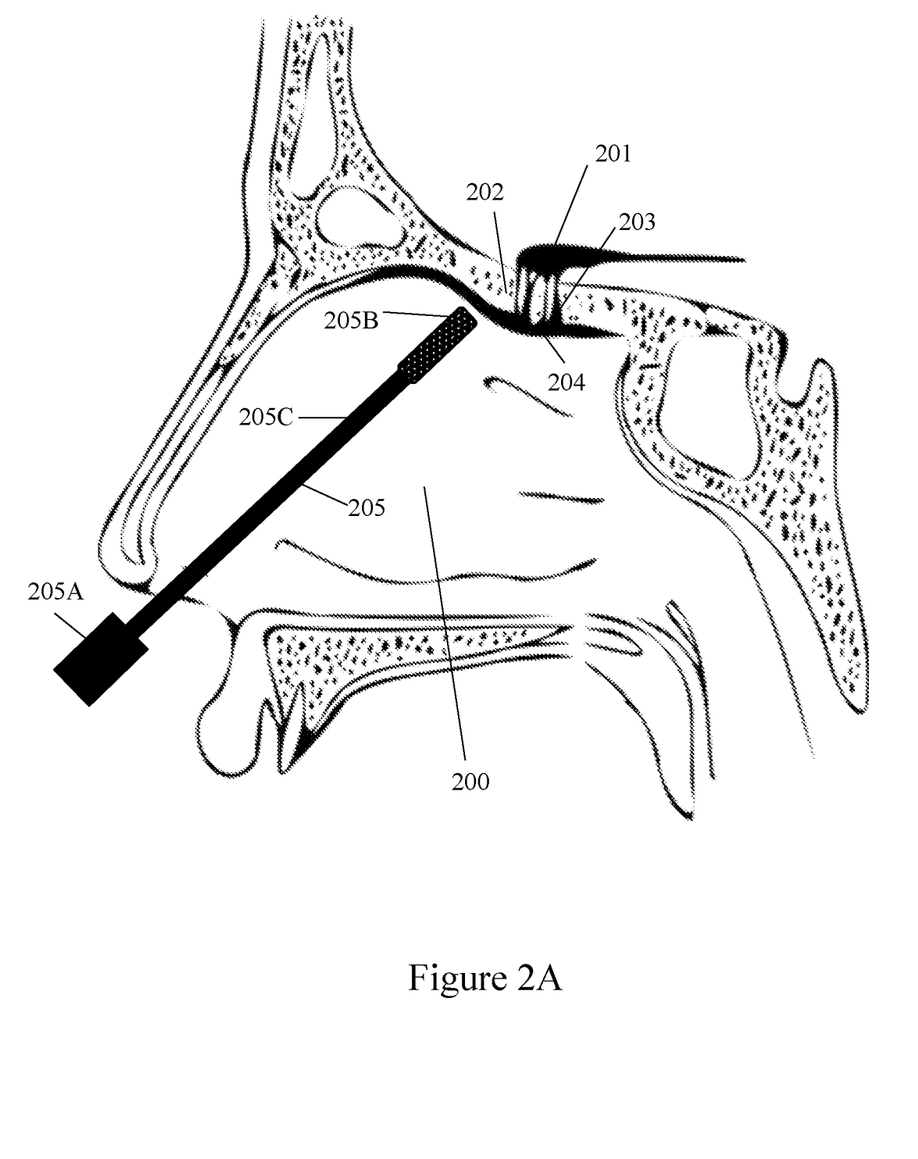
FIG. 2A shows a configuration of the device where the distal end is in collapsed state and FIG. 2B shows the distal end of the device expanded.
Figure 2B:
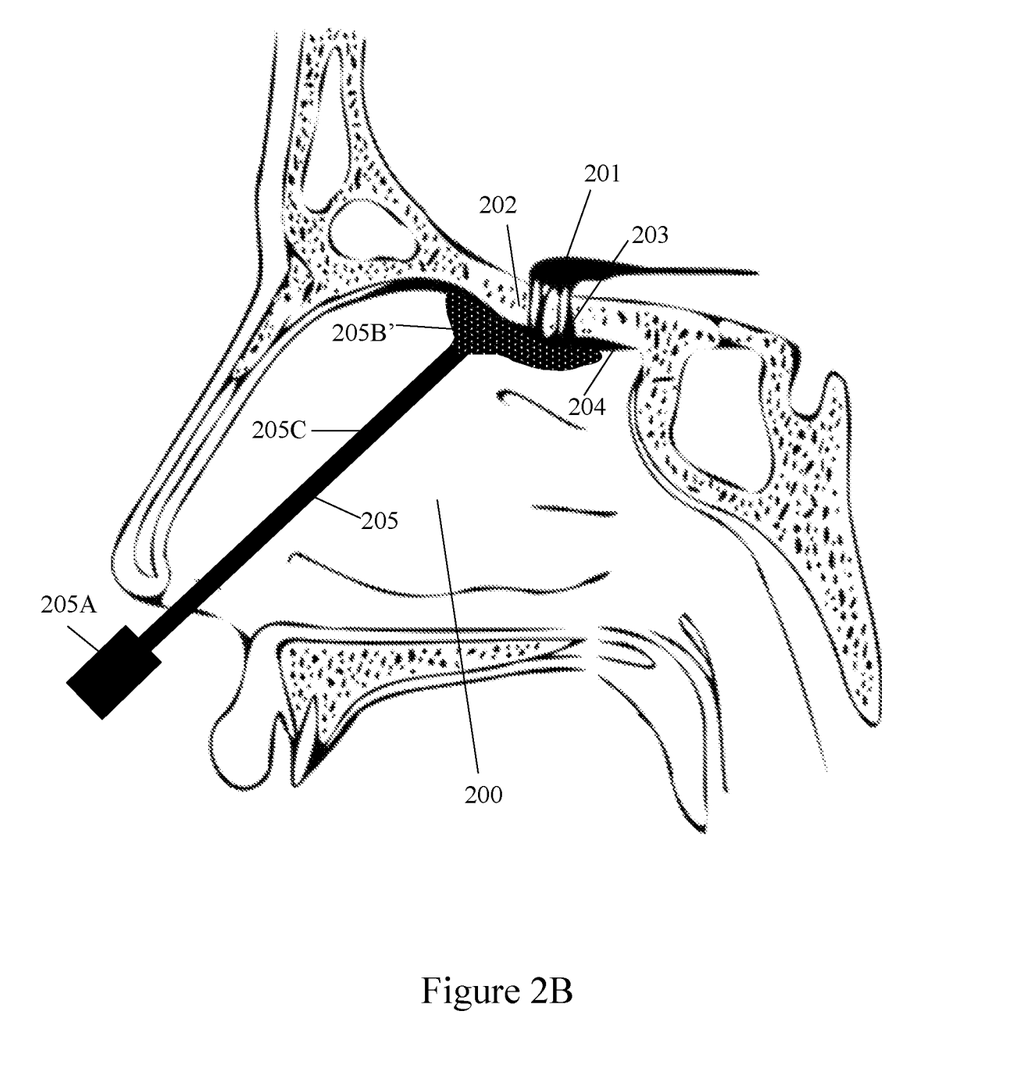

FIG. 2A depicts patient anatomy, including the nasal cavity 200, olfactory bulb 201, cribriform plate 202, primary olfactory neurons 203, and olfactory mucous membrane 204. Device 205 may be comprised of proximal end 205A connected to the distal end 205B by elongated shaft 205C. In this embodiment the distal end 205B is in a collapsed format while navigating though the nasal cavity 200. FIG. 2B depicts nasal cavity 200, olfactory bulb 201, cribriform plate 202, primary olfactory neurons 203, and olfactory mucous membrane 204. Once device 205 reaches the proximity of the mucous membrane 204 covering the cribriform plate 202, collapsed distal end 205B is expanded to distal end 205B'. Expanded distal end 205B' meets the mucosal membrane 204 and ablates the target tissue. The expanded format of distal end 205B' allows it to cover and conform to the shape of the tissue to be ablated. Once the ablation procedure completes expanded distal end 205B' is collapsed to distal end 205B to facilitate navigation of device 205 out of nasal cavity 200.

In another embodiment the device 205 has cryogenic component that uses compressed gas or liquid as a refrigerant. In this embodiment the expansion of the refrigerant gas or liquid inside device 205 causes the cooling of the distal end 205B. In this embodiment the refrigerant gas used to cool cryogenic device 205 may be used to expand the distal end from configuration 205B to configuration 205B'. Once the flow of the refrigerant gas or liquid into device 205 is stopped, device 205 warms to environmental temperatures and distal end 205B' deflates to distal end 205B and device 205 is navigated out of nasal cavity 200.

In another embodiment device 205 may use two or more different mechanisms to expand distal end 205B and to ablate olfactory neurons 203. As an example embodiment, device 205 may use saline injection to expand distal end 205B to distal end 205B' and radiofrequency energy to ablate olfactory neurons 203.

In another embodiment the expandable component of distal end 205B is a balloon. In yet another embodiment the expandable component of distal end 205B is an expandable structure made of thermally conductive materials such as metals or shape memory alloys.

Figure 3:
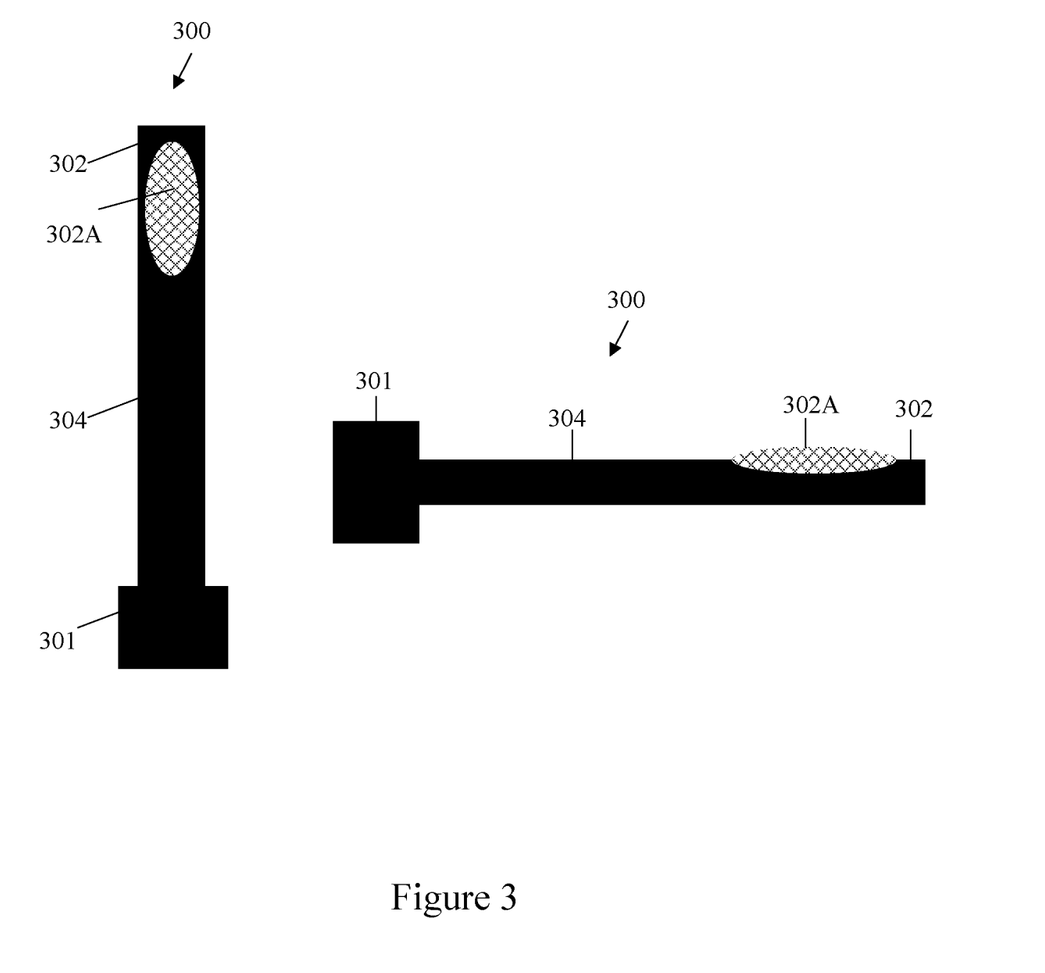
FIG. 3 is a schematic of the device from front and side views where only a portion of the distal end is an ablation effector.

FIG. 3 depicts device 300 comprising proximal end 301, distal end 302 and elongated shaft 304. In this embodiment only a portion of distal end 302, section 302A, is capable of effecting tissue ablation. As olfactory mucosa is located in tight areas of nasal cavity, having only section 302A to effect ablation ensures other nearby structures are not affected by the procedure. The section 302A is illustrated in the embodiment shown as being located along a single side of the shaft 304 near or at the distal end 302. The section 302A may alternatively be formed along a section of the circumference or entirely around the circumference of the shaft 304. In another alternative, the section 302A may instead be formed as multiple sections separated from one another rather than a single continuous portion. Other configurations which may provide partial ablation along selected tissue regions are also contemplated.

In an example of the embodiment above, device 300 is a cryogenic device and section 302A is made of expandable material capable of expanding using the cryogenic refrigerant gas or liquid, in this example section 302A comes in contact with target tissue causing localized ablation.

Figure 4:
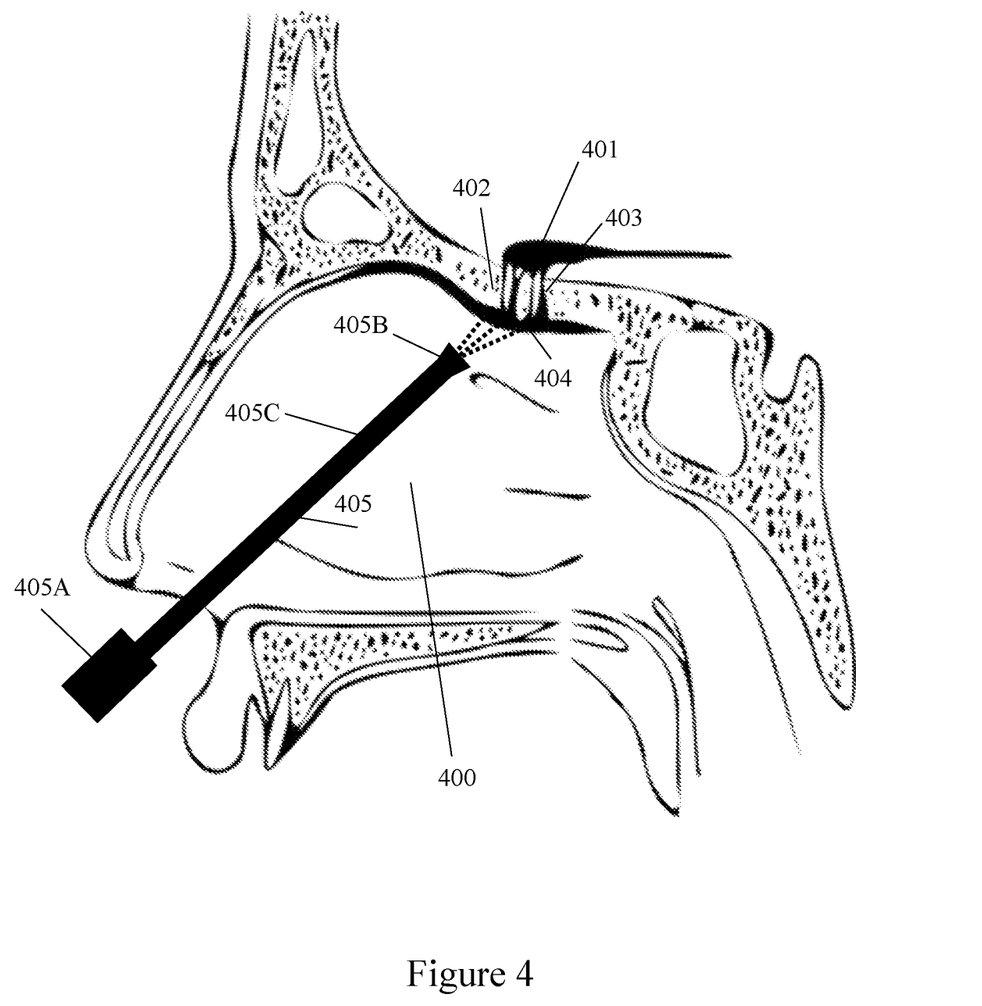
FIG. 4 illustrates the position of the olfactory apparatus within the nasal cavity and a schematic of an example of the device, where the distal end includes a spraying instrument.

FIG. 4 depicts patient anatomy, including nasal cavity 400, olfactory bulb 401, cribriform plate 402, primary olfactory neurons 403, and olfactory mucous membrane 404. Device 405 is comprised of proximal end 405A connected to the distal end 405B by elongated shaft 405C. In this embodiment distal end 405B has a spray component capable of spraying liquid or gas ablation material directly on the target tissue. In another configuration of this embodiment device 400 is a cryogenic device and distal end 405B sprays cryogenic material directly on target tissue to effect ablation. In another example the device 400 sprays chemicals capable of inducing tissue ablation directly on the target tissue. Examples of such chemicals include ethanol, phenol, and zinc sulphate, etc.

In yet another example device 400 is used to spray therapeutic agents directly unto the target tissue. In one example the therapeutic agent is capable of selectively ablating primary olfactory neurons 405, sparing other components of the olfactory mucosa 404. Example of such therapeutic agents include capsaicin and its analogues, including but not limited to Zucapsaicin, ALGRX-4975, Nonivamide, Resiniferatoxin, or combinations thereof, or sympatholytic agents such as alpha- and beta-adrenergic receptor antagonists (alpha blockers and beta blockers) as well as centrally acting agents such as clonidine, guanabenz, methyldopa, minoxidil, and reserpine.

In another embodiment distal end 405B is an injection needle capable of injecting liquid chemicals or therapeutic agents directly into olfactory mucous membrane 404. Such liquid chemicals or therapeutic agents are capable of effecting ablation once injected. Examples of chemicals used for ablation include ethanol, phenol, zinc sulphate and examples of therapeutic agents include capsaicin and its analogues.

Figure 5:
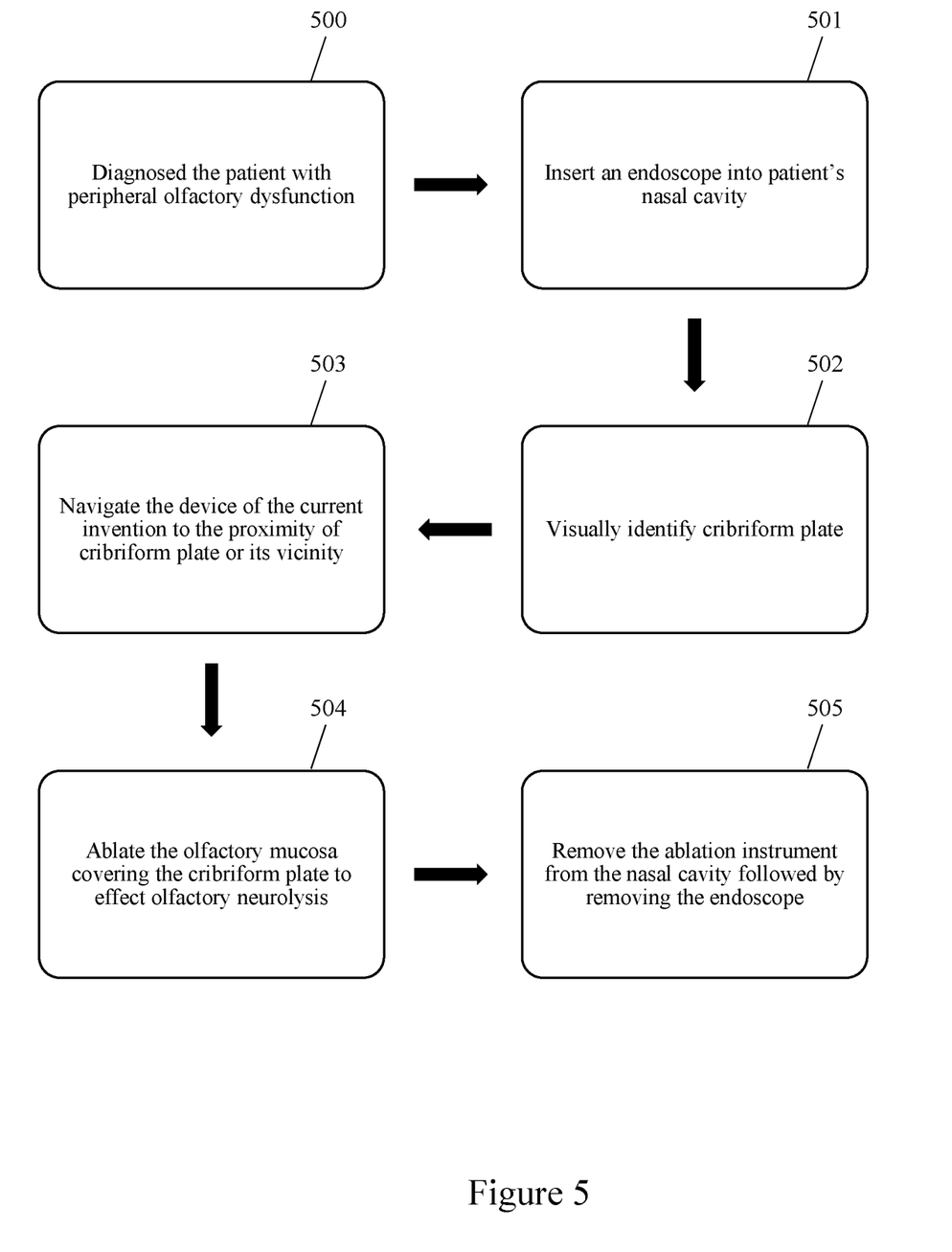
FIG. 5 illustrates the method of treating an olfactory dysfunction in a patient by ablating olfactory nerves using the devices disclosed.

FIG. 5 shows a flowchart that incorporates olfactory ablation in the management of a patient with peripheral olfactory dysfunction. Initially treating physician consults with the patient to ensure the dysfunction is of peripheral origin 500. This can be done for example by temporary blocking of the primary olfactory neurons with numbing medication such as lidocaine or cocaine. If the numbing completely resolves the dysfunction, for example in case of parosmia and phantosmia, resolve the presence of the phantom smell, it is determined that the dysfunction is of peripheral origin. Other techniques or procedures can be used for different dysfunctions to ascertain the peripheral nature of the issue.

After the patient is deemed a candidate for the procedure 500, olfactory ablation may be performed by first inserting an endoscope into the nasal cavity 501. The endoscope contains an optical or visual system that allows the physician to see into the nasal cavity. With this optical or visual system, the physician identifies the cribriform plate 502. Alternatively, if the device includes a visualization component, the device itself may be introduced into the nasal cavity directly without a separate endoscope. In yet another alternative, the device may be introduced simultaneously with a separate endoscope or in yet another alternative, the device may be introduced without an endoscope or with an external imaging device.

The device of the current invention is then inserted through the nasal cavity and navigated to the proximity of the cribriform plate and the olfactory mucous membrane 503. The device may include an endoscope for visualization and navigation eliminating the need for the use of an additional endoscope. In one embodiment, the device is navigated to the target with assistance from navigation systems.

The device is then used to ablate the primary olfactory neurons using various ablative technologies examples of which include cryogenic ablation, radiofrequency ablation, laser ablation, chemical ablation, etc. 504. The ablation procedure will cause olfactory neurolysis and effectively destroy some or substantially all of the targeted neurons. Multiple ablations can be optionally performed to increase the efficacy of the procedure. Once the ablation procedure is complete, the device is navigated proximally out of the patient's nasal cavity followed by removing the endoscope if one is used 505.

With olfactory ablation, the patient may experience a cessation in his or her existing sense of smell including the olfactory dysfunction such as phantosmia. New olfactory neurons regenerate over the course of several months, and with that regeneration may come a return of the patient's sense of smell Additional ablation procedures might be necessary to completely resolve the issue.

The ablation procedure described in the present invention can be followed by additional treatment modalities, for example local administration of stem cells, growth factors, or anti-inflammatory agents to accelerate or modulate the regeneration of neurons.

The applications of the devices and methods discussed above are not limited to the treatments described but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method for treating peripheral olfactory dysfunction in a patient, comprising:
    introducing a treatment device into a nasal cavity of the patient having at least one symptom of olfactory dysfunction, the treatment device having a proximal end, a distal end, an elongated shaft therebetween, and a treatment end effector disposed on or near the distal end;
    advancing the distal end of the treatment device into proximity of a cribriform plate within the nasal cavity;
    conforming the treatment end effector to a surface of an olfactory mucosa; and
    ablating at least one olfactory neuron through the surface of the olfactory mucosa and via the treatment end effector to reduce at least one symptom of olfactory dysfunction.

2. The method of claim 1, wherein treating peripheral olfactory dysfunction comprises treating for hyperosmia, normosmia, hyposmia, anosmia, parosmia, or phantosmia.

3. The method of claim 1, wherein ablating at least one olfactory neuron comprises ablating the at least one olfactory neuron via a cryogenic agent to effect nerve ablation.

4. The method of claim 1, wherein the treatment device has a length of 4 cm to 12 cm.

5. The method of claim 4, wherein the distal end has a diameter of 0.5 mm to 5 mm and a length of 2 mm to 30 mm.

6. The method of claim 1, wherein ablating the at least one olfactory neuron comprises freezing the at least one olfactory neuron to a temperature of between −20° C. to −100° C.

7. The method of claim 1, wherein ablating the at least one olfactory neuron comprises ablating at least one neuron via radiofrequency energy, pulsed radiofrequency energy, laser, microwave energy, or chemicals to effect ablation.

8. The method of claim 1, further comprising introducing a visualization instrument into the nasal cavity prior to ablating the at least one olfactory neuron.

9. The method of claim 1, wherein introducing the treatment device comprises imaging the nasal cavity via a navigation aid while advancing the distal end of the treatment device within the nasal cavity prior to ablating the at least one olfactory neuron.

10. The method of claim 1, wherein advancing the distal end of the treatment device further comprises reconfiguring a treatment structure to transition from a collapsed configuration to a deployed configuration.

11. The method of claim 10, further comprising reconfiguring the structure to conform against the surface of the olfactory mucosa.

12. The method of claim 1 wherein treating peripheral olfactory dysfunction in the patient comprises treating the patient to regenerate a sense of smell by the patient.

13. A method for treating peripheral olfactory dysfunction in patient, comprising:
    introducing a treatment device into a nasal cavity of the patient having at least one symptom of olfactory dysfunction, the treatment device having a proximal end, a distal end, an elongated shaft therebetween, and a spray component disposed on or near the distal end;
    advancing the distal end of the treatment device into proximity of at least one olfactory neuron associated with olfactory mucosa; and
    spraying at least one chemical upon a surface of the olfactory mucosa to ablate the at least one olfactory neuron within the olfactory mucosa to reduce at least one symptom of olfactory dysfunction.

14. The method of claim 13, wherein treating peripheral olfactory dysfunction comprises treating for hyperosmia, normosmia, hyposmia, anosmia, parosmia, or phantosmia.

15. The method of claim 13, wherein spraying the at least one chemical comprises spraying phenol, ethanol, or zinc sulphate.

16. The method of claim 13, wherein spraying the at least one chemical comprises spraying a cryogenic agent.

17. The method of claim 13, wherein spraying the at least one chemical comprises spraying a chemical selected from the group consisting of capsaicin or its analogues, Zucapsaicin, ALGRX-4975, Nonivamide, Resiniferatoxin, and combinations thereof.

18. The method of claim 13, wherein spraying the at least one chemical comprises spraying a sympatholytic agent such as alpha- and beta-adrenergic receptor antagonists (alpha blockers and beta blockers), centrally acting agents such as clonidine, guanabenz, methyldopa, minoxidil, and reserpine and combinations thereof.

19. The method of claim 13, wherein spraying the at least one chemical comprises spraying a neurotoxin.

20. The method of claim 13, further comprising introducing a visualization instrument into the nasal cavity prior to spraying the at least one chemical.

21. The method of claim 13, wherein introducing the treatment device comprises imaging the nasal cavity via a navigation aid while advancing the distal end of the treatment device within the nasal cavity prior to spraying the at least one chemical.

22. The method of claim 13, wherein advancing the distal end of the treatment device further comprises reconfiguring a treatment structure to transition from a collapsed configuration to a deployed configuration.

23. A method for treating peripheral olfactory dysfunction in patient, comprising:
    introducing a treatment device into a nasal cavity of the patient having at least one symptom of olfactory dysfunction, the treatment device having a proximal end, a distal end, an elongated shaft therebetween, and an injection instrument disposed on or near the distal end;
    advancing the distal end of the treatment device into proximity of at least one olfactory neuron associated with olfactory mucosa; and
    injecting at least one chemical into the olfactory mucosa to ablate the at least one olfactory neuron within the olfactory mucosa to reduce at least one symptom of olfactory dysfunction.

24. The method of claim 23, wherein treating peripheral olfactory dysfunction comprises treating for hyperosmia, normosmia, hyposmia, anosmia, parosmia, or phantosmia.

25. The method of claim 23, wherein injecting the at least one chemical comprises injecting phenol, ethanol, or zinc sulphate.

26. The method of claim 23, wherein injecting the at least one chemical comprises injecting a chemical selected from the group consisting of capsaicin or its analogues, Zucapsaicin, ALGRX-4975, Nonivamide, Resiniferatoxin, and combinations thereof.

27. The method of claim 23, wherein injecting the at least one chemical comprises injecting a neurotoxin.

28. The method of claim 23, wherein injecting the at least one chemical comprises injecting a sympatholytic agent selected from the group consisting of alpha- and beta-adrenergic receptor antagonists (alpha blockers and beta blockers), centrally acting agents such as clonidine, guanabenz, methyldopa, minoxidil, and reserpine, and combinations thereof.

29. The method of claim 23, further comprising introducing a visualization instrument into the nasal cavity prior to injecting the at least one chemical.

30. The method of claim 23, wherein introducing the treatment device comprises imaging the nasal cavity via a navigation aid while advancing the distal end of the treatment device within the nasal cavity prior to injecting the at least one chemical.

* * * * *